United States Patent
Simonson

Patent Number: 5,885,285
Date of Patent: *Mar. 23, 1999

[54] SPINAL IMPLANT CONNECTION ASSEMBLY

[76] Inventor: Peter Melott Simonson, 770 Claughton Island Dr., Suite 414, Miami, Fla. 33131

[*] Notice: The term of this patent shall not extend beyond the expiration date of Pat. No. 5,047,029.

[21] Appl. No.: 775,705

[22] Filed: Dec. 16, 1996

Related U.S. Application Data

[63] Continuation-in-part of Ser. No. 515,289, Aug. 14, 1995, Pat. No. 5,643,263.

[51] Int. Cl.$^6$ .................................................. A61B 17/57
[52] U.S. Cl. .................................. 606/61; 606/72; 606/73
[58] Field of Search .................................. 606/60, 61, 69, 606/72, 73

[56] References Cited

U.S. PATENT DOCUMENTS

| | | |
|---|---|---|
| 3,317,225 | 5/1967 | Cooper . |
| 4,611,582 | 9/1986 | Duff . |
| 4,614,452 | 9/1986 | Wang . |
| 4,738,252 | 4/1988 | Friddle et al. . |
| 4,827,918 | 5/1989 | Olerud . |
| 5,002,542 | 3/1991 | Frigg . |
| 5,013,085 | 5/1991 | Craig . |
| 5,041,112 | 8/1991 | Mingozzi et al. . |
| 5,047,029 | 9/1991 | Aebi et al. . |
| 5,053,034 | 10/1991 | Olerud . |
| 5,057,109 | 10/1991 | Olerud . |
| 5,092,867 | 3/1992 | Harms et al. . |
| 5,108,395 | 4/1992 | Laurain . |
| 5,108,397 | 4/1992 | White . |
| 5,190,390 | 3/1993 | Ming-Tai . |
| 5,254,118 | 10/1993 | Mirkovic . |
| 5,261,909 | 11/1993 | Sutterlin et al. . |
| 5,312,404 | 5/1994 | Asher et al. . |
| 5,320,623 | 6/1994 | Pennig . |
| 5,344,422 | 9/1994 | Frigg . |
| 5,376,090 | 12/1994 | Pennig . |
| 5,423,818 | 6/1995 | Van Hoeck et al. . |
| 5,443,465 | 8/1995 | Pennig . |
| 5,443,467 | 8/1995 | Biedermann et al. . |
| 5,443,515 | 8/1995 | Cohen et al. . |

OTHER PUBLICATIONS

TSRH® Pedicle Screw Spinal System—Severe Spondylolisthesis of L5–S1 Grade 3 & 4, Surgical Technique (Brochure).
TSRH® Spinal System—Design Rationale (Brochure).
TSRH® Pedical Screw System (Brochure).

*Primary Examiner*—Michael Buiz
*Assistant Examiner*—Daphna Shai
*Attorney, Agent, or Firm*—Quarles & Brady LLP

[57] ABSTRACT

A connection assembly for connecting a spinal implant rod to a spinal implant bolt includes a rod connecting member having an opening for receiving a portion of the rod, and a bolt connecting member having an opening for receiving a portion of the bolt. The rod connecting member and bolt connecting member are rotatably engaged to one another. At least one interface washer is positioned over and between the rod connecting member and the bolt connecting member. Structure for creating a force between the rod, the rod connecting member, the washer, the bolt, and the bolt connecting member is provided. The interface washer has structure for engaging at least one of the rod and the rod connecting member, and for engaging at least one of the bolt and the bolt connecting member, so as to prevent relative rotation of the rod and the rod connecting member and the bolt and the bolt connecting member when the force is applied.

10 Claims, 5 Drawing Sheets

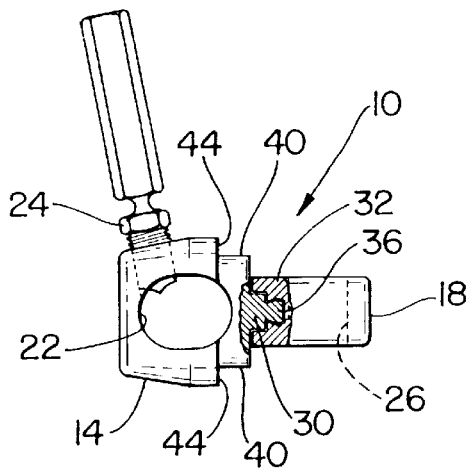
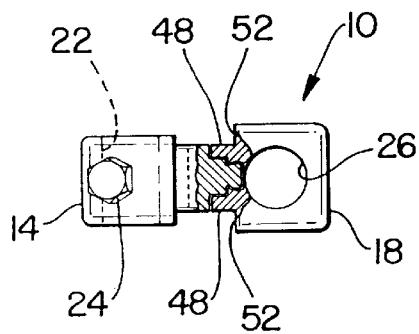
FIG. 1
FIG. 2
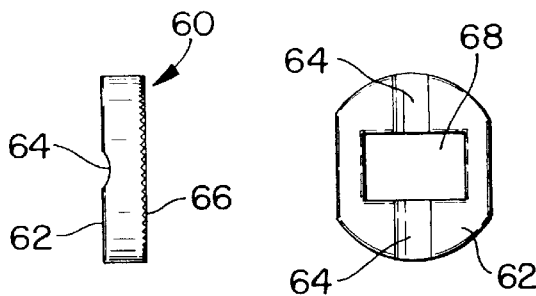
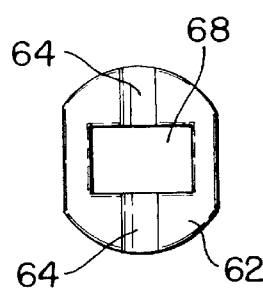
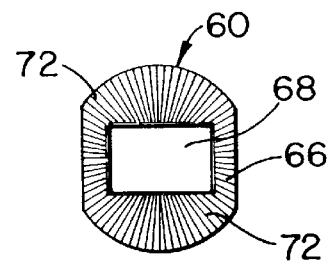
FIG. 3
FIG. 4
FIG. 5
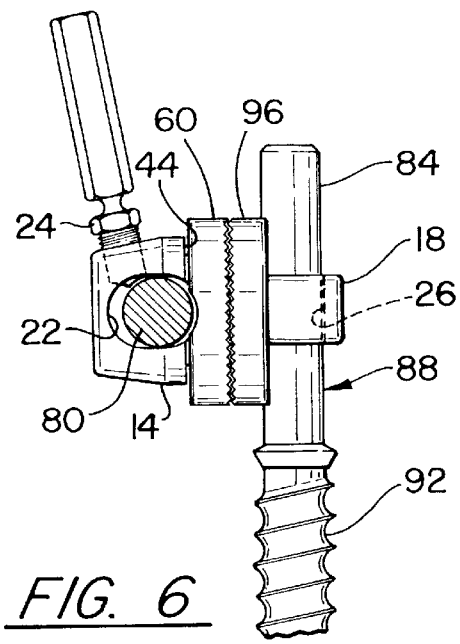
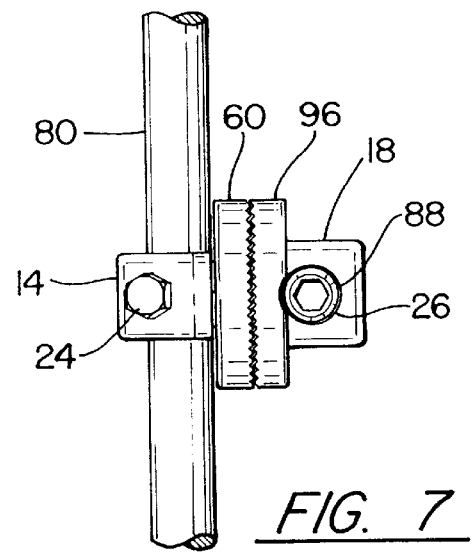
FIG. 6
FIG. 7

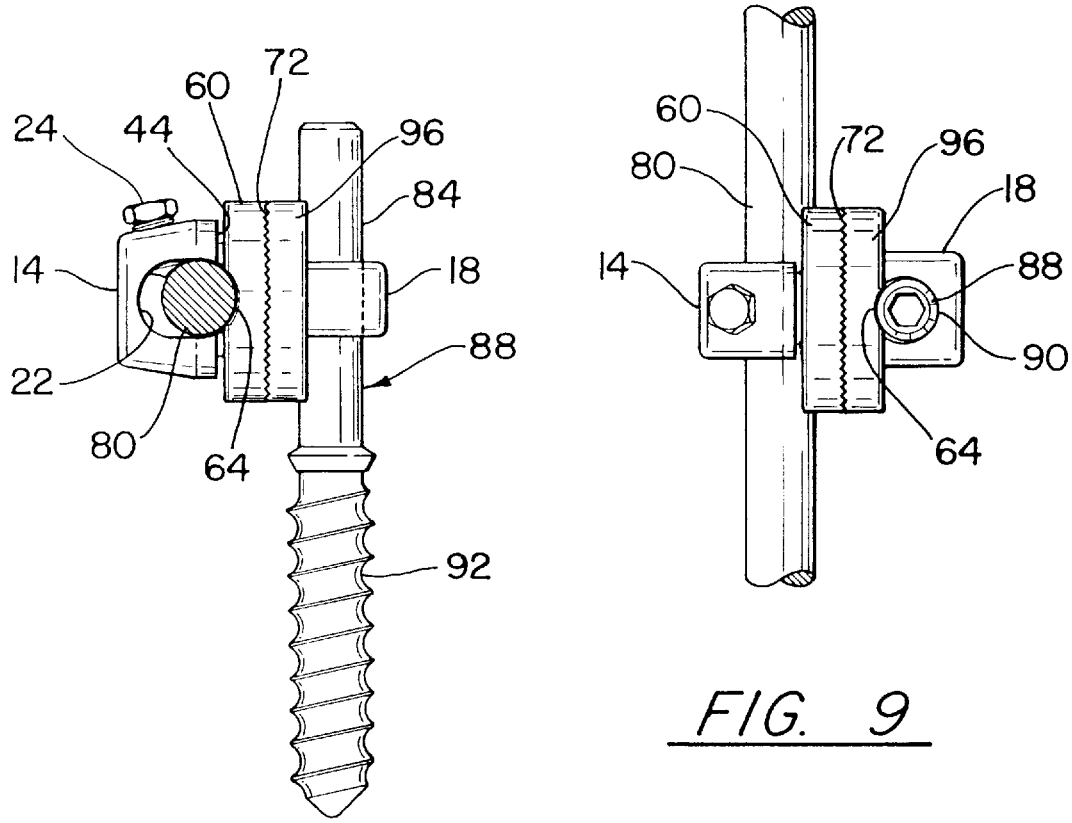
FIG. 8
FIG. 9
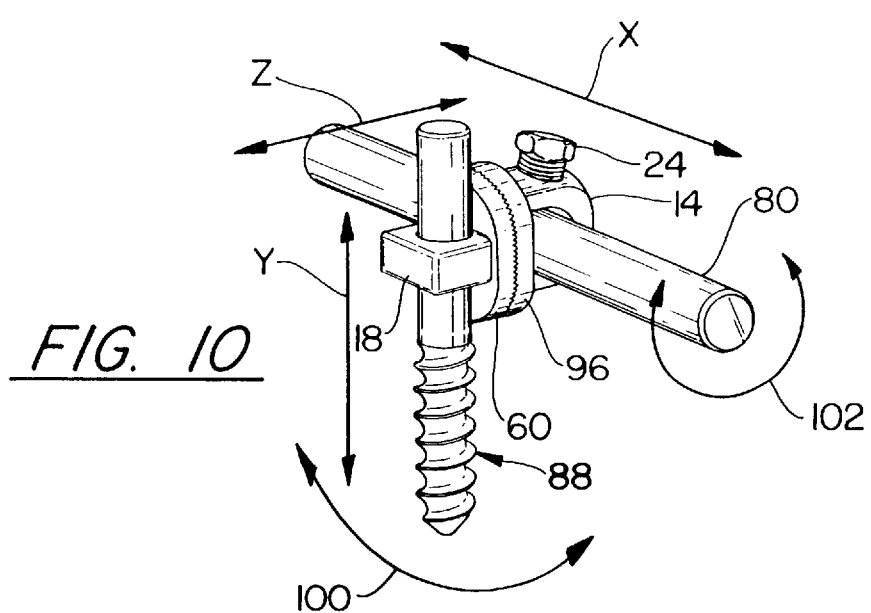
FIG. 10

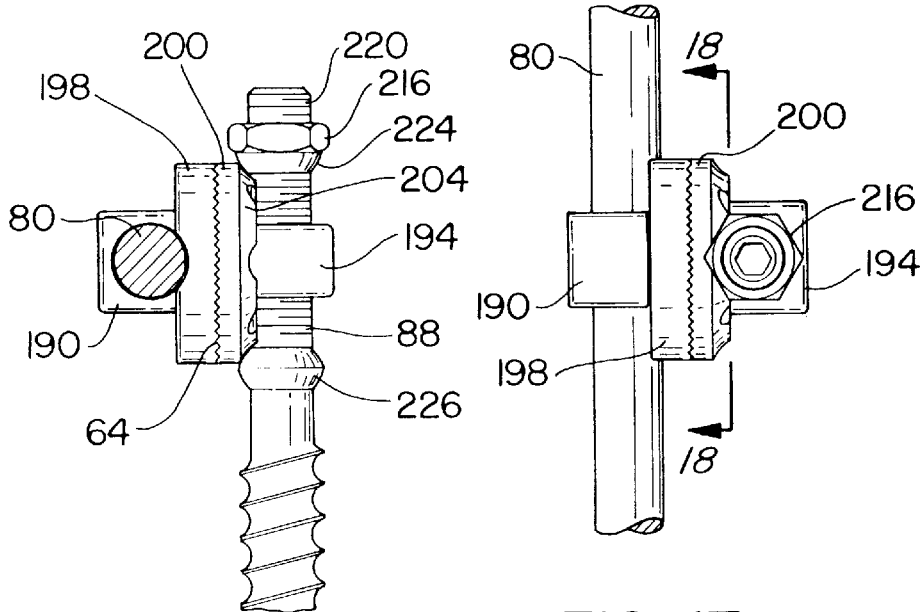
FIG. 16
FIG. 17
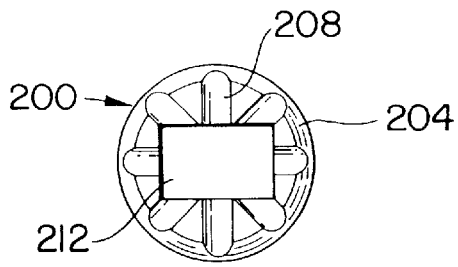
FIG. 18
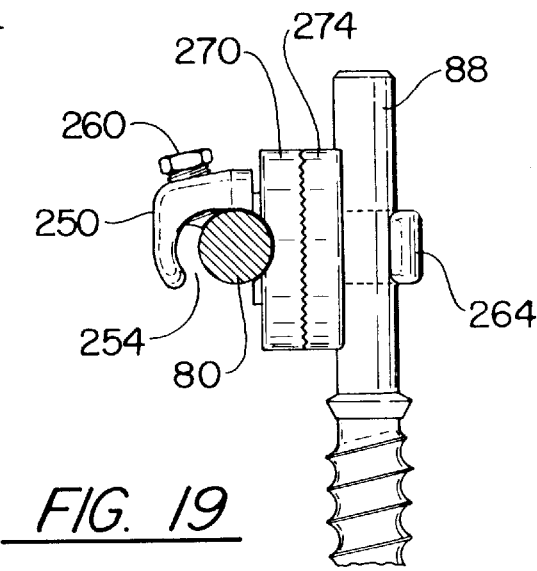
FIG. 19
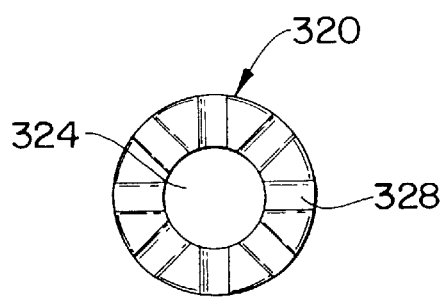
FIG. 20

SPINAL IMPLANT CONNECTION ASSEMBLY

CROSS REFERENCE TO RELATED APPLICATION

This application is a continuation-in-part application of Applicant's U.S. patent application Ser. No. 08/515,289, filed Aug. 14, 1995 U.S. Pat. No. 5,643,263.

FIELD OF THE INVENTION

This invention relates generally to a spinal implant assembly, and more particularly to a spinal implant connection assembly.

BACKGROUND OF THE INVENTION

Spinal implant systems provide a rod for supporting the spine and properly positioning components of the spine for various treatment purposes. Bolts or screws are typically secured into the vertebrae for connection to the supporting rod. These bolts must frequently be positioned at various angles due to the anatomical structure of the patient, the physiological problem, and the preference of the physician. It is difficult to provide secure connection between the spinal support rod and these connecting bolts at various angles, and where there are differing distances between the rod and bolts and different heights relative to these components.

SUMMARY OF THE INVENTION

It is an object of the invention to provide a connection assembly which will securely engage a spinal support rod to connecting bolts.

It is a further object of the invention to provide a connection assembly which will provide for engagement of the spinal support rod to the connecting bolts where the connecting bolts are at a variety of angles relative to the vertical, taken when the patient is lying down.

It is yet another object of the invention to provide a connection assembly which will allow connection between a spinal support rod and connecting bolts at a variety of vertical and horizontal distances between the rod and bolts.

These and other objects are accomplished by a connection assembly for connecting a spinal implant rod to a spinal implant bolt which includes a rod connecting member having an aperture for receiving a portion of the rod and a bolt connecting member having an aperture for receiving a portion of the bolt. The rod connecting member and bolt connecting member are rotatably engaged to one another. A rod interface washer is positioned over a portion of the rod connecting member, and a bolt interface washer is positioned over a portion of the bolt connecting member. The rod interface washer and bolt interface washer are moveable in part between the rod connecting member and the bolt connecting member, the rod connecting washer being fixed against rotation relative to the rod connecting member and the bolt interface washer being fixed against rotation relative to the bolt interface washer. Structure extendable into at least one of the apertures is provided, so as to urge one of the rod and bolt toward the other, and to cause the washers to be pressed together between the rod and the bolt, preventing rotation of the rod interface washer and rod connecting member relative to the bolt interface washer and bolt connecting member, and securing the rod to the bolt.

In another embodiment, a slide-in pin assembly is used to rotatably engage the rod connecting member to the bolt connecting member. A partially open clasp can replace the enclosed aperture of the rod connecting member and/or the bolt connecting member.

In another embodiment of the invention, a wedge nut is used to urge the interface washer away from the bolt and toward the rod. The rod will be pressed outwardly against the rod connecting member and the bolt will be pressed outwardly against the bolt connecting member.

In another embodiment, a single washer takes the place of the rod interface washer and the bolt interface washer. This compound washer has engagement structure such as grooves on each side for engaging the rod and the bolt so as to prevent relative rotation of the rod connecting member and the bolt connecting member.

BRIEF DESCRIPTION OF THE DRAWINGS

There are shown in the drawings embodiments which are presently preferred, it being understood, however, that the invention is not limited to the precise arrangements and instrumentalities shown, wherein:

FIG. 1 is a front elevation of a rod connecting member and bolt connecting member according to the invention, partially in phantom.

FIG. 2 is a plan view.

FIG. 3 is a front elevation of an interface washer according to the invention.

FIG. 4 is a side elevation.

FIG. 5 is an opposite side elevation.

FIG. 6 is a front elevation, partially in cross-section and partially in phantom, of a connection assembly according to the invention in a positioning mode.

FIG. 7 is a plan view, partially broken away and partially in phantom.

FIG. 8 is a front elevation, partially in cross section and partially in phantom, of a connection assembly according to the invention in a secured mode.

FIG. 9 is a plan view, partially broken away and partially in phantom.

FIG. 10 is a perspective view.

FIG. 16 is a front elevation, partially broken away, of a connection assembly according to still another alternative embodiment.

FIG. 17 is a top plan view.

FIG. 18 is a side elevation viewed from line 18—18 in FIG. 17.

FIG. 19 is a front elevation, partially broken away and partially in phantom, of another embodiment.

FIG. 20 is a side elevation of an interface washer according to an alternative embodiment.

DETAILED DESCRIPTION OF THE PREFERRED EMBODIMENTS

Figure 11:
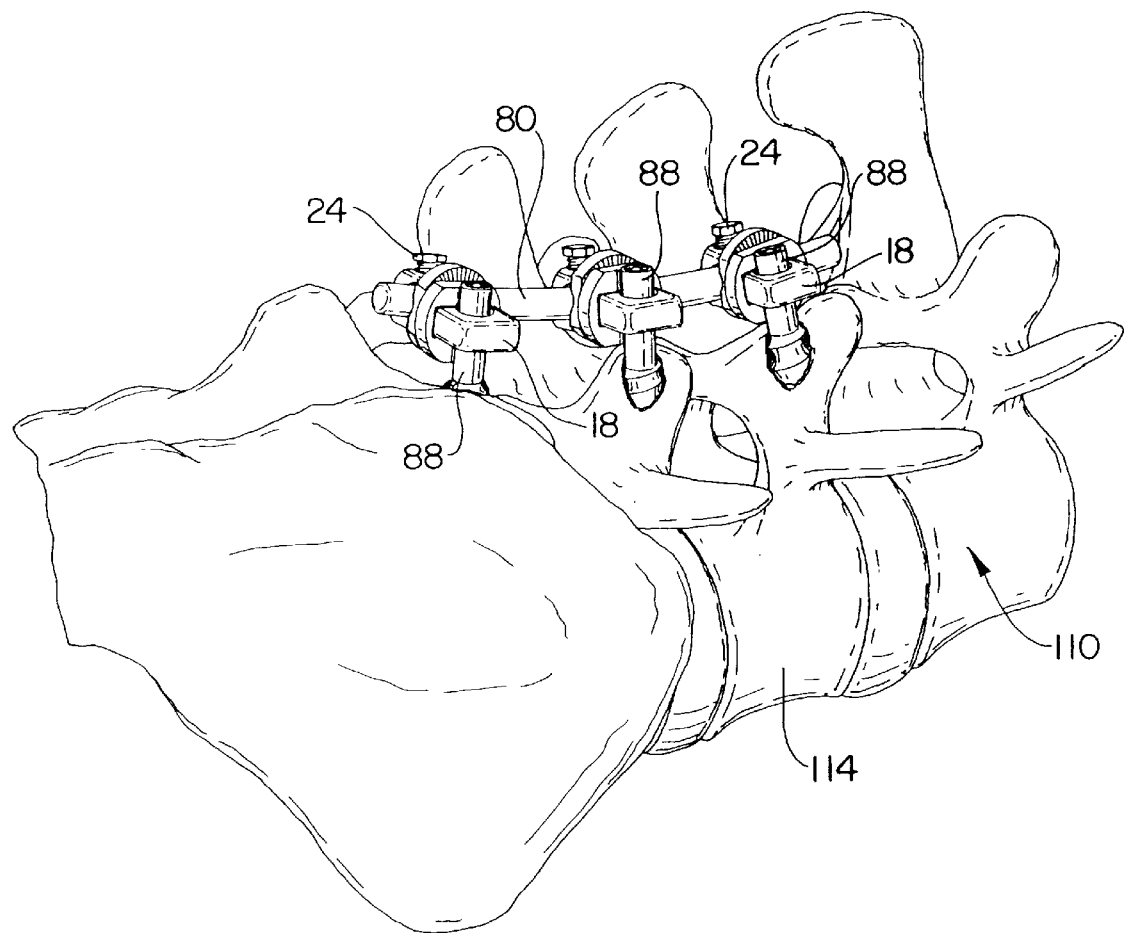
FIG. 11 is a perspective view of a connection assembly according to the invention in a secured mode in a spinal column.
Figures 12, 13:
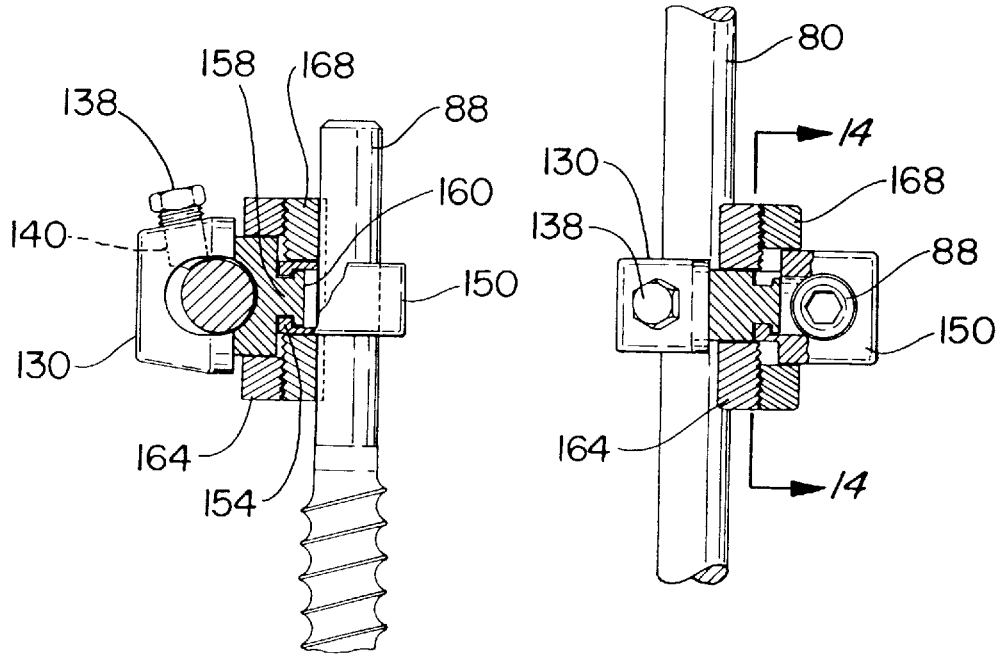
FIG. 12 is a front elevation, partially broken away and partially in phantom, of a connection assembly according to an alternative embodiment of the invention.
FIG. 13 is a top plan view, partially broken away.
Figure 14:
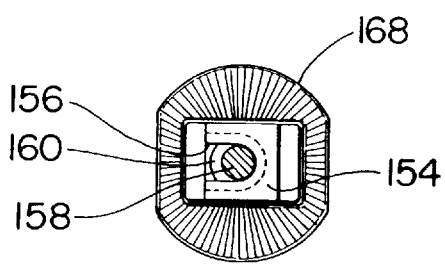
FIG. 14 is a section taken along line 14—14 in FIG. 13.
Figure 15:
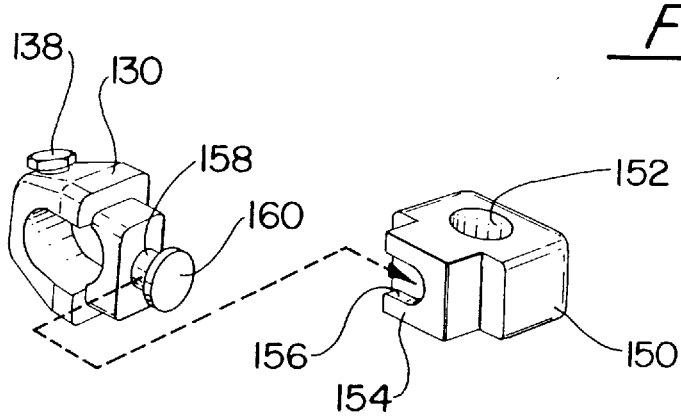
FIG. 15 is an exploded perspective of an alternative connection assembly according to the invention.

There is shown in FIGS. 1–2 a spinal implant connection assembly 10 according to the invention. The swivel assembly connection 10 comprises a rod connecting member 14 and a bolt connecting member 18. The rod connecting member 14 has an aperture 22 for receiving a rod in a spinal implant system. Structure for urging the rod within the aperture 22, such as the set screw 24, is provided through a suitable threaded opening in the rod connecting member 14 so as to be extendable into the aperture 22. The bolt connecting member 18 has an aperture 26 for receiving a bolt or screw of a spinal implant system.

The rod connecting member 14 and bolt connecting member 18 are attached by a rotatable connection. The rotatable connection can be of any suitable design. It is preferable that the swivel connection have a snap-together construction to facilitate the assembly of the final device. In one suitable design, the rod connecting member 14 can have a male protrusion 30 and the bolt connecting member 18 can have a corresponding female cavity formed in a neck 32. A flared end portion 36 of the male protrusion 30 can be provided to cooperate with a corresponding portion of the female cavity to provide snap-in engagement. The male protrusion 30 is preferably symmetrical about its long axis to facilitate rotation in the female cavity, and will thereby provide a swivel connection between the rod connecting member 14 and the bolt connecting member 18.

Alternatively, the male and female connections could be provided by a threaded member, such as a screw, and a threaded opening in one of the rod connecting member 14 and the bolt connecting member 18. The screw would extend through an opening in one of the rod connecting member 14 and bolt connecting member 18 to connect to the threaded opening in the other member, so as to rotatably engage the two members together.

The rod connecting member 14 can have a washer seat portion 40. A seat that is substantially rectangular in cross section is currently preferred, but the seat 40 can be of any suitable shape. A washer stop surface 44 can be provided by an enlarged portion of the rod connecting member 14. The bolt connecting member can have a washer seat 48 and a similar washer stop surface 52.

An interface washer 60 according to the invention is shown in FIGS. 3–5. The interface washer can be any of several suitable shapes, including the semi-oval shape that is depicted. One surface of the interface washer 60 has an engagement surface 62, which preferably has an engagement groove 64 for engaging a cylindrical rod, bolt or screw surface. The engagement groove 64 runs substantially diametrically through the oval washer. A central opening 68 in the washer corresponds in shape to the cross-sectional shape of the respective washer seat to which it is engaged, whether the washer seat 40 of the rod connecting member 14 or the washer seat 48 of the bolt connecting member 18. In the currently preferred embodiment, the corresponding openings and washer seats are of substantially rectangular shape, although this shape could vary and be of varying size, and could also be different for the washer seat 40 of the rod connecting member 14 and the washer seat 48 of the bolt connecting member 18.

The interface washer 60 has a washer connection surface 66 opposite to the engagement surface 62. The washer connection surface 66 preferably includes structure for facilitating the engagement of the washer against rotational movement relative to another interface washer against which it is pressed. This engagement structure is preferably a plurality of variable angle ridges 72 which radiate from the rotational center of the interface washer 60, as will be explained below.

The complete rotatable connection assembly 10 is shown in FIGS. 6–7. A rod 80 is positioned in the aperture 22 of the rod connecting member 14. A post 84 of a bolt 88 that is connected to a screw portion 92 is positioned through the aperture 26 of the bolt connecting member 18. It will be appreciated that the screw 92 is typically oriented somewhat vertically into the spine when the patient is lying horizontally. The rod 80 extends somewhat horizontally along the length of the spine of the patient, again when the patient is lying.

Two interface washers 60 are provided with the connection assembly of the invention. A first interface washer 60 is provided over the washer seat 40 of the rod connecting member 14. A second interface washer 96, preferably similar in construction to the interface washer 60, is positioned over the washer seat 48 of the bolt connecting member 18. The washer connection surfaces 66 of each washer face one another in the completed assembly. In the present embodiment, the bolt interface washer 96 is substantially identical to the rod interface washer 60, and includes an engagement groove 64, an opening 68, and variable angle surfaces 72. The variable angle surfaces 72 of the rod interface washer 60 and the bolt interface washer 96 face one another in the assembled swivel connection assembly. This permits mutual engagement of the rod interface washer 60 and the bolt interface washer 96.

The rod interface washer 60 and bolt interface washer 96 are oriented substantially 180° to one another because of the orientation of the rod connecting member 14 and bolt connecting member 18. The width of the interface washers 60 and 96 is less than the distance between the respective washer stop surface 44 of the rod connecting member 14 and the washer stop surface 52 of the bolt connecting member 18. There is therefore some freedom of movement of the interface washers 60 and 96 between the rod connecting member 14 and bolt connecting member 18. Also, because the variable angle surfaces 72 are non-engaged, the rod connecting member 14 and rod interface washer 60 can rotate freely with respect to the bolt connecting member 18 and the bolt interface washer 96.

The aperture 22 of the rod connecting member 14 and aperture 26 of the bolt connecting member 18 are larger in dimension than the cross section of the rod 80 and bolt 88, such that movement of each within the respective aperture is possible. The flexibility of the invention in making a connection between the rod 80 and a plurality of bolts 88 is provided because the swivel assembly can be moved up and down over the portion 84 and horizontally over the rod 80, as can be seen from FIGS. 6–7. The rod 80 and bolt 88 can be in differing angular positions, because the rod connecting member 14 and bolt connecting member 18 can rotate relative to each other. Finally, the linear distance between the rod 80 and bolt 88 can be adjusted because of the variability provided by the apertures 22 and 26. Also, different sizes of spinal implant connection assemblies 10 according to the invention can be provided, and with different thicknesses of interface washers 60 and 96, such that differing distances between the rod 80 and bolt 88 can be accommodated.

The manner of connection of the spinal implant connection assembly 10 according to the invention to the rod 80 and the bolt 88 is depicted in FIGS. 8–11. When the rod connecting member 14 and bolt connecting member 18 have been properly positioned over the rod 80 and bolt 88, it is necessary to tighten the connection to retain this position. This is accomplished by use of the set screw 24. The set screw 24 is threaded into the aperture 22 (FIG. 8) where it contacts the side of the rod 80 and forces the rod 80 toward the bolt connecting member 18. The rod 80 contacts the rod interface washer 60, and preferably engages the engagement groove 64 as previously described. This will force the rod interface washer 60 against the bolt interface washer 96. The variable angle surfaces 72 of each will engage to prevent further rotation of the rod connecting member 14 and bolt connecting member 18 relative to one another, because the rod interface washer 60 and bolt interface washer 96 are fixed relative to the respective rod connecting member 14 and bolt connecting member 18. The assembly becomes unitary and cannot swivel when they are engaged. As the set screw 24 is threaded further into the cavity 22, the rod interface washer 60 and bolt interface washer 96 are forced further toward the bolt 88. The bolt 88 is engaged by the bolt interface washer 96, preferably by an engagement groove 64. This will force the bolt 88 against a lateral surface 90 of the aperture 26 to secure the bolt 88 in place. The entire assembly will thereby become locked against movement. Adjustments can be made by loosening the set screw 24 and then re-tightening the set screw when the preferred position has been located.

The advantages of the invention are shown in FIG. 10. An X, Y, and Z axis are illustrated for purposes of reference. Prior to fixation, the bolt connecting member 18 can move along the Y axis by sliding over the bolt 88. It can be seen that rotation about the Y axis is also possible, since the bolt connecting member 14 can rotate around the bolt 88, as illustrated by the arrow 100. The assembly can be moved along the X axis because the rod connecting member 14 can slide over the rod 80 prior to fixation. The assembly can be rotated about the X axis, as illustrated by the arrow 102, because the rod connecting member 14 can rotate around the rod 80. The assembly can be moved along the Z axis because either or both of rod connecting member 14 and the bolt connecting member 18 can permit respective movement of the rod 80 and/or the bolt 88 in the aperture of each. The set screw 24 can be used to fix the assembly in place at the desired position along the Z axis. The assembly is capable of rotation about the Z axis because the rod connecting member 14 and the bolt connecting member 18 are rotatably engaged to one another. The invention thereby provides for omnidirectional adjustment while in place during an operation, and permits both active and passive translational and rotational adjustments without additional washers or nuts.

The connection assembly as installed in a spinal column 110 is shown in FIG. 11. The bolts 88 are inserted into the vertebrae 114 in the position that is desired by the surgeon. The rod 80 is bent so as to align with the bolts 88. It can be seen from FIG. 11 that precise alignment of the rod 80 with the differing heights and relative angles of the bolts 88 is difficult. The invention provides flexibility in the connection of the rod 80 to the bolts 88 by permitting relative height adjustment of the rod 80 to the bolts 88, angular adjustment about the X and Y axes (FIG. 10) and linear adjustment about the X, Y and Z axes. The set screws 24 are tightened by the surgeon when the desired position is obtained to secure the connection assembly in position.

The manner by which the rod connecting member 14 is rotatably secured to the bolt connecting member 18 is also capable of variations. Rivets, screws, pivot pins and various male-female connections are also possible. An alternative connection assembly is shown in FIGS. 12–15. According to this embodiment, a rod connecting member 130 has an aperture 134 adapted to receive the rod 80. Suitable fastening structure such as the set screw 138 can be provided in a threaded opening 140 to urge the rod 80 within the aperture 134. A bolt connecting member 150 has an aperture 152 adapted to receive the bolt 88. The bolt connecting member 150 has an end which terminates in an extension 154 which has an open-ended slot 156. A pin 158 that is connected to the rod connecting member 130 has a head 160 which is adapted to fit behind the slot 156 and engage the slotted extension 154 in the manner depicted in FIGS. 14–15. This will rotatably engage the rod connecting member 130 to the bolt connecting member 150. A rod interface washer 164 and a bolt interface washer 168 are provided. The rod interface washer 164 and bolt interface washer 168 include suitable engagement structure such as grooves by which relative rotation of the washers is prevented when the washers are pressed together. The rod interface washer 164 does not rotate relative to the rod connecting member 130, and the bolt interface washer 168 does not rotate relative to the bolt connecting member 150. Tightening of the set screw 138 will urge the rod 80 against the rod interface washer 164. This will cause the rod interface washer 164 to engage the bolt interface washer 168 which in turn will engage the bolt 88 and cause the bolt 88 to engage the bolt connecting member 150. The rod interface washer 164 and bolt interface washer 168, when secured in position, will also cover the open-ended slot 156 to prevent the slippage of the pin 158 out of the slot 156.

Yet another embodiment of the invention is shown in FIGS. 16–18. In this embodiment, the rod 80 is positioned through a suitable aperture in rod connecting member 190. The bolt 88 is positioned through a suitable aperture or opening in a bolt connecting member 194. As previously described, the rod connecting member 190 and bolt connecting member 194 are rotatably engaged to one another. A rod interface washer 198 is provided and does not rotate relative to the rod connecting member 190. A bolt interface washer 200 is provided and does not rotate relative to the bolt connecting member 194. The rod interface washer 198 and bolt interface washer 200 can have suitable engagement structure such as grooves 64 so that, when pressed together, relative rotation of the rod interface washer 198 with respect to the bolt interface washer 200, and also rotation of the rod connecting member 190 relative to the bolt connecting member 194, is prevented.

The bolt interface washer 200 has a beveled surface 204. A series of radial grooves 208 can be provided on the bolt interface washer 200 to engage the bolt 88. A central opening 212 is provided to fit over a portion of the bolt connecting member 194. A wedge nut 216 includes a threaded opening for threaded movement on the threads 220 of the bolt 88. A wedge surface 224 is provided on a lower depending side of the wedge nut 216.

In operation, after the rod 80 has been positioned relative to the bolt 88 and the connection assembly has been properly positioned, the wedge nut 216 is tightened. This will cause the wedge surface 224 of the wedge nut 216 to contact the beveled surface 204 of the bolt interface washer 200. Continued downward movement of the wedge nut 216 will cause the bolt interface washer 200 to press against the rod interface washer 198, which will force the rod 80 into engagement with the rod connecting member 190. The force between the rod interface washer 198 and bolt interface washer 200 will cause engagement of the grooves 64 to secure the rod interface washer 198 from rotation relative to the bolt interface washer 200 so as to fix the relative position of the rod connecting member 190 to the bolt connecting member 194. The bolt 88 will be urged against the bolt connecting member 194. The grooves 208 will serve to engage the bolt 88 so as to prevent rotation. A protrusion 226 on the bolt 88 is contacted by the bolt interface washer 200 as the wedge nut 216 is urged downward so as to prevent downward slippage of the connection assembly from the desired position.

The invention is capable of taking other alternative forms. It is not necessary that the rod connecting member and bolt connecting member have an aperture for receiving the rod and/or bolt. A partially open channel or other suitable structure can alternatively be used, so long as the rod connecting member is capable of fixing the rod, and that fixation of the rod will occur with contact between the rod and at least one washer. In FIG. 19 there is shown a connection assembly in which a rod connecting member 250 is substantially J-shaped. The rod 80 fits into the open channel 254 and is secured in place by suitable structure such as set screw 260. The bolt 88 similarly fits into an open channel formed by a substantially J-shaped bolt connecting member 264. A rod interface washer 270 and bolt interface washer 274 are provided as previously described.

The rod interface washer and bolt interface washer can be replaced by a single interface washer 320. The single interface washer 320 according to this embodiment of the invention is shown in FIG. 20. The interface washer includes a large central opening 324 and a plurality of radially directed grooves 328 on each side of the washer. The washer will be in contact with both the rod 80 and bolt 88, with the grooves 328 engaging each, so that an engagement between the rod, washer, and the bolt is created and the rod 80 is fixed in space relative to the bolt 88.

The bolt 88 that is illustrated in the drawings is a common device that is used to secure a rod to the spine. It will be appreciated by those skilled in the art that the invention has utility with other securing devices such as pins, rods, hooks, cylinders, screws and snaps. These devices are commonly cylindrical, but can also be elliptical, rectangular, and other shapes.

The invention is capable of taking a number of specific forms without departing from the spirit or essential attributes thereof. Accordingly, reference should be had to the following claims, rather than the foregoing specification, as indicating the scope of the invention.

I claim:

1. A connection assembly for connecting a spinal implant rod to a spinal implant device, the assembly comprising:
    a connection unit including a rod connecting portion having an opening for receiving a portion of the rod, and a bolt connecting portion having an opening for receiving a portion of the bolt and for permitting translational movement over the bolt, the rod connecting portion and the bolt connecting portion being rotatably engaged to one another;
    at least one interface washer positioned over and between the rod connecting portion and the bolt connecting portion, the interface washer being moveable in part between the rod connecting portion and the bolt connecting portion; and
    means extendable into the opening of at least one of the rod connecting portion and the bolt connecting portion, for urging one of the rod and the bolt toward the other, whereby the interface washer will be pressed by one of the rod and the bolt toward the other, causing said interface washer to operatively engage the rod and the bolt against rotation relative to said interface washer, preventing rotation of the rod and the rod connecting portion relative to the bolt and the bolt connecting portion, and securing the rod to the bolt.

2. The connection assembly of claim 1, wherein at least one of the rod connecting member and bolt connecting member comprises a washer seat and washer stop for permitting sliding movement of the interface washer over a portion of the respective opening, said stop surface preventing removal of the interface washer from the respective connecting member.

3. The connection assembly of claim 1, wherein the rod connecting member and the bolt connecting member are rotationally engaged by corresponding male protrusion and female cavity portions.

4. The connection assembly of claim 1, wherein said interface washer comprises an engagement groove.

5. The connection assembly of claim 1, wherein the at least one interface washer comprises means for fixing the interface washer against rotation relative to the rod and means for fixing the interface washer against rotation relive to the bolt.

6. A method for connecting a rod to a securing device in a spinal implant system for a patient, comprising the steps of:
    providing a spinal implant rod and at least one securing device such as a bolt;
    providing a connection assembly with a connection unit comprising a rod connecting portion having an opening for receiving a portion of the rod, a bolt connecting portion having an opening for receiving a portion of the bolt and for permitting translational movement over the bolt, the rod connecting portion and the bolt connecting portion being rotatably engaged to one another, said connection assembly further comprising at least one interface washer positioned over and between the rod connecting portion and the bolt connecting portion, the at least one interface washer being moveable in part between the rod connecting portion and the bolt connecting portion and being fixed against rotation relative to at least one of the rod connecting portion and the bolt connecting portion; and means for creating a force between the rod, the rod connecting portion, the washer, the bolt, and the bolt connecting portion, so as to prevent relative rotation of the rod and the rod connecting portion and the bolt and the bolt connecting portion;
    positioning the rod connecting portion over the desired portion of the rod;
    positioning the bolt connecting portion over the desired portion of the bolt;
    creating a force with said force creating means to urge said at least one washer into operative engagement with at least one of the rod and rod connecting portion, and with at least one of the bolt and bolt connecting portion, preventing rotation of the rod and rod connecting portion relative to the bolt and bolt connecting portion.

7. The method of claim 6, wherein, in the step of providing a connection assembly, the at least one interface washer comprises means for engaging at least one of the rod and the rod connecting portion, and for engaging at least one of the bolt and the bolt connecting portion.

8. A connection assembly for connecting a spinal implant rod to a securing device such as a spinal implant bolt, the assembly comprising:
    a rod connecting portion having an opening for receiving a portion of the rod and a bolt connecting portion having an opening for receiving a portion of the bolt and for permitting translational movement over the bolt, the rod connecting portion and the bolt connecting portion being rotatably engaged to one another;

at least one interface washer positioned over and between the rod connecting portion and the bolt connecting portion;

means for creating a force between the rod, the rod connecting portion, the washer, the bolt, and the bolt connecting portion, so as to prevent relative rotation of the rod and the rod connecting portion and the bolt and the bolt connecting portion.

9. The connection assembly of claim 8, wherein said force is applied by a wedge nut screwed onto a spinal implant bolt, said wedge nut contacting said interface washer.

10. The connection assembly of claim 8, wherein the at least one interface washer comprises means for engaging at least one of the rod and the rod connecting portion, and for engaging at least one of the bolt and the bolt connecting portion.

* * * * *

UNITED STATES PATENT AND TRADEMARK OFFICE
CERTIFICATE OF CORRECTION

PATENT NO.    : 5,885,285
DATED         : March 23, 1999
INVENTOR(S)   : Peter M. Simonson It is certified that error appears in the above-identified patent and that said Letters Patent is hereby corrected as shown below:

<u>Title page,</u>
Item [*], please delete the patent number "5,047,029" and insert -- 5,643,263 -- in its place.

Signed and Sealed this

Twenty-ninth Day of January, 2002

Attest:

JAMES E. ROGAN
*Attesting Officer*  *Director of the United States Patent and Trademark Office*